United States Patent [19]

Sorenson et al.

[11] 4,429,577
[45] Feb. 7, 1984

[54] ULTRASONIC TRANSDUCER SYSTEM WITH FLUID APPLICATOR

[75] Inventors: Paul D. Sorenson, Blaine; Dale A. Dickson, Fridley, both of Minn.

[73] Assignee: Medtronic, Inc., Minneapolis, Minn.

[21] Appl. No.: 414,702

[22] Filed: Sep. 3, 1982

[51] Int. Cl.³ .............................................. G01N 29/00
[52] U.S. Cl. ...................................... 73/644; 310/336
[58] Field of Search ........................... 73/644; 310/336

[56] References Cited

U.S. PATENT DOCUMENTS

| | | | |
|---|---|---|---|
| 2,724,783 | 11/1955 | Renaut | 310/336 |
| 3,323,354 | 6/1967 | Daubresse et al. | 73/644 |
| 3,420,097 | 1/1969 | Batterman et al. | 73/644 |
| 3,958,451 | 5/1976 | Richardson | 73/644 |
| 4,012,946 | 3/1977 | Patsey et al. | 73/644 |
| 4,242,912 | 1/1981 | Burckhardt et al. | 73/626 |
| 4,245,250 | 1/1981 | Tiemann | 358/140 |
| 4,246,791 | 1/1981 | Glenn | 73/620 |
| 4,252,026 | 2/1981 | Robinson | 73/626 |
| 4,253,338 | 3/1981 | Iinuma et al. | 73/626 |
| 4,265,121 | 5/1981 | Cribbs | 73/607 |
| 4,271,706 | 6/1981 | Ledley | 73/614 |
| 4,271,842 | 6/1981 | Specht et al. | 128/661 |
| 4,272,991 | 6/1981 | Cribbs | 73/621 |

*Primary Examiner*—Howard A. Birmiel
*Attorney, Agent, or Firm*—Robert J. Klepinski; John L. Rooney; Joseph F. Breimayer

[57] ABSTRACT

An ultrasonic transducer system for scanning a body including an ultrasonic transducer mounted in a transducer shoe and means for applying acoustic coupling fluid to the transducer/body interface as the shoe moves along the interface. The means for applying the coupling fluid includes a fluid reservoir and a fluid dispensing channel in the transducer shoe, a position transducer for producing a signal proportional to the movement of the dispensing means along the transducer/body interface, a microprocessor responsive to the signal, and a stepping motor driven pump controlled by the microprocessor to pump fluid from the fluid reservoir to the dispensing channel in an amount determined by the movement of the dispensing means along the ultrasonic transducer/body interface.

6 Claims, 5 Drawing Figures

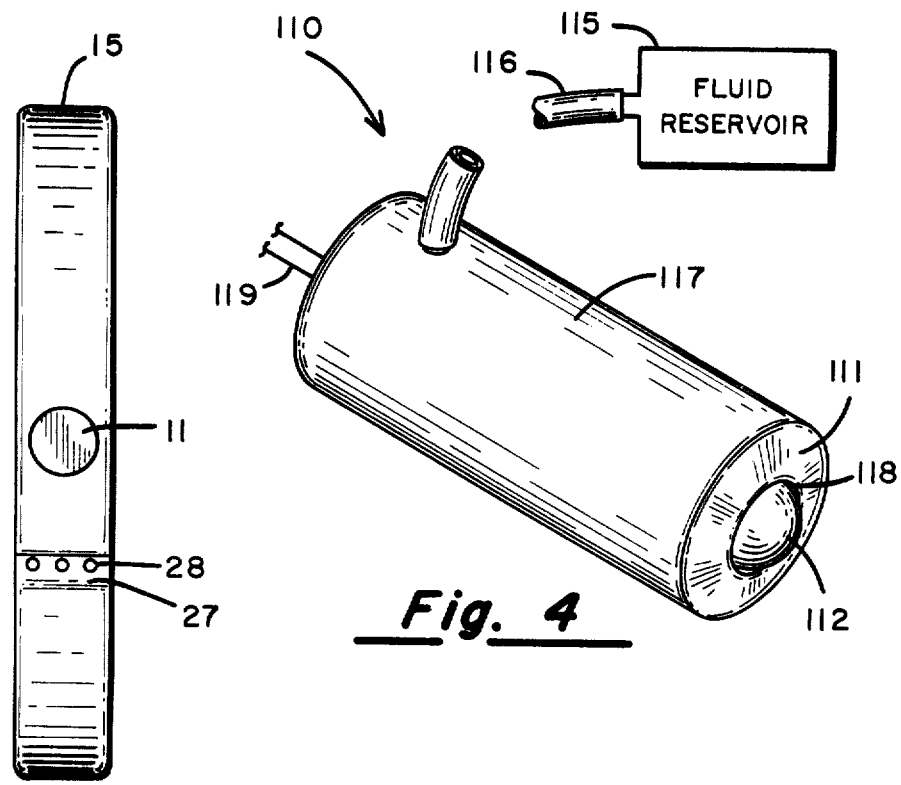
Fig. 3
Fig. 4
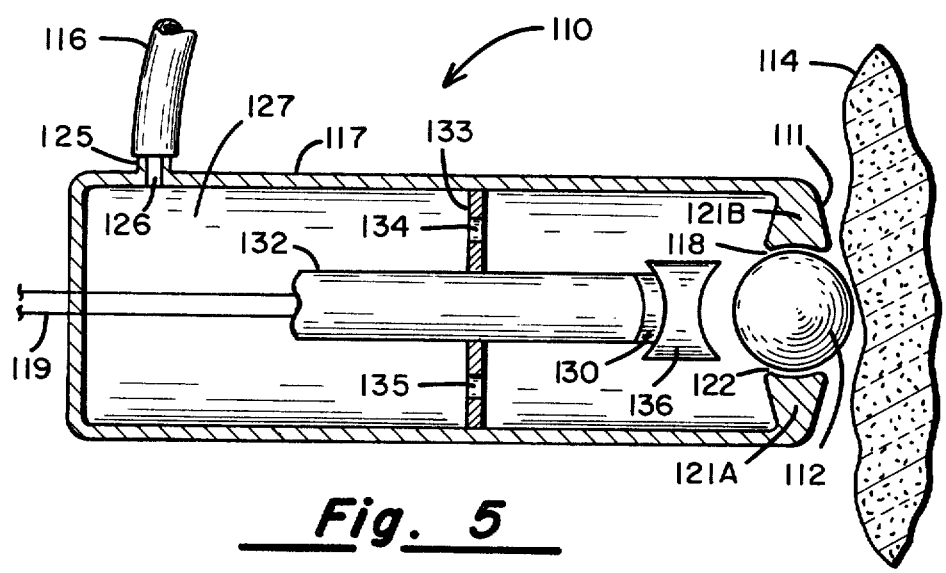
Fig. 5

ULTRASONIC TRANSDUCER SYSTEM WITH FLUID APPLICATOR

BACKGROUND OF THE INVENTION

1. Field of the Invention

This invention in general relates to the field of ultrasonic imaging, and more particularly concerns an improved ultrasonic imaging system that automatically dispenses the proper amount of acoustic coupling fluid as an ultrasonic transducer moves along the object to be scanned.

2. Description of the Prior Art

In recent years ultrasonic imaging has become important in many areas of medical diagnosis, as for example, in obstetrics, cardiology, and the detection of tumors. Generally, in the ultrasonic imaging process, an ultrasonic camera or, what we shall refer to herein as an ultrasonic imaging module, is placed against and/or moved over the surface of the patient's body, or other object the interior of which it is desired to image. U.S. Pat. No. 4,246,791 describes an example of such a module. Generally, in the trade, the term "transducer" is ambiguously applied to the entire ultrasonic "camera" or imaging module, to the piezoelectric element in which electrical energy is transformed into vibrating energy, and also to various portions of the system, depending on the viewpoint. For clarity, in this disclosure we shall refer to the ultrasonic "camera" as an ultrasonic imaging module, and shall use the term "transducer" to designate that portion of the camera that actually vibrates. The piezoelectric element in which the energy is transformed from electrical to vibrational shall be referred to as the "transducer element". Of course, in some instances, the transducer and the transducer element may be one and the same.

In order to obtain a meaningful ultrasonic image it is necessary that the interface between the ultrasonic imaging module and the patient be predictable, repeatable, and conductive to the transmission of the ultrasonic energy with minimal distortion. Generally, an acoustic coupling fluid such as Aquasonic Scan ®, Parker Labs, Inc., Orange, N.J. 07050 is applied to the surface of the patient's body to provide the desired interface. In the prior art, the acoustic coupling fluid has been applied by hand, which results in varying amount of the fluid being applied, which may lead to erratic transmission of the ultrasonic energy across the interface. Further, this is messy and time-consuming, and sometimes may not be done for these reasons which results in inefficient coupling of the transducer to the body. Therefore, it would be highly desirable to provide an ultrasonic imaging system that overcomes these problems.

SUMMARY OF THE INVENTION

It is an object of the invention to provide an ultrasonic imaging system that automatically applies the proper amount of acoustic coupling fluid to the surface of the body as an ultrasonic transducer passes over it.

It is a further object of the invention to provide an ultrasonic imaging system that automatically dispenses an amount of acoustic coupling fluid proportional to the surface area of the body scanned by the module.

It is a further object of the invention to provide an ultrasonic imaging system that provides one or more of the above objects and, at the same time, is characterized by improved ultrasonic coupling at the transducer/body interface.

Finally, it is an object of the invention to provide an ultrasonic imaging system which provides one or more of the above objects and, at the same time, overcomes one or more of the disadvantages at prior art imaging modules.

The invention provides an ultrasonic transducer system for scanning the body, the system including a module of the type having a transducer for converting electrical energy to a beam of ultrasonic energy and for converting received ultrasonic energy to an electrical signal and a means for conducting electrical energy to and from the transducer, the transducer being supported in a housing. The system includes a source of acoustic coupling fluid, and a means connected to the source for applying the fluid to the interface between the transducer and the body in an amount related to the surface area of the body scanned by the module. Preferably there is a means connected to the source and located on the exterior of the housing for dispensing the fluid, and a means for regulating the flow of fluid between the source and the means for dispensing. In one aspect of the invention the means for dispensing includes a bearing in the housing, a roller-ball mounted in the bearing, a chamber within the housing for containing fluid, with the roller-ball forming a portion of the wall of the chamber, and a channel between the bearing and the roller-ball of a size such that the fluid does not pass through the channel when the roller-ball is not rotating, and the fluid passes the channel when the roller-ball rotates. In another aspect of the invention, the means for regulating includes a position transducer and an A/D converter responsive to the movement of the means for dispensing along the transducer/body interface for producing a signal representative of the movement, a microprocessor responsive to the signal for producing a plurality of electrical pulses, a pump for pumping the acoustic coupling fluid from the reservoir to the means for dispensing and a stepping motor or other electromechanical servo mechanism responsive to the microprocessor pulses for driving the pump. Numerous other features, objects and advantages of the invention will become apparent from the following detailed description when read in conjunction with the accompanying drawings.

BRIEF DESCRIPTION OF THE DRAWINGS

In the drawing:

FIG. 3 is a front view of the transducer shoe of the module of FIG. 1;

FIG. 4 is a perspective view of an alternative embodiment of a transducer module according to the invention; and FIG. 5 is a partially cross-sectioned side view of the transducer module of FIG. 4 shown being applied to the surface of a body;

DESCRIPTION OF THE PREFERRED EMBODIMENT

Figure 1:
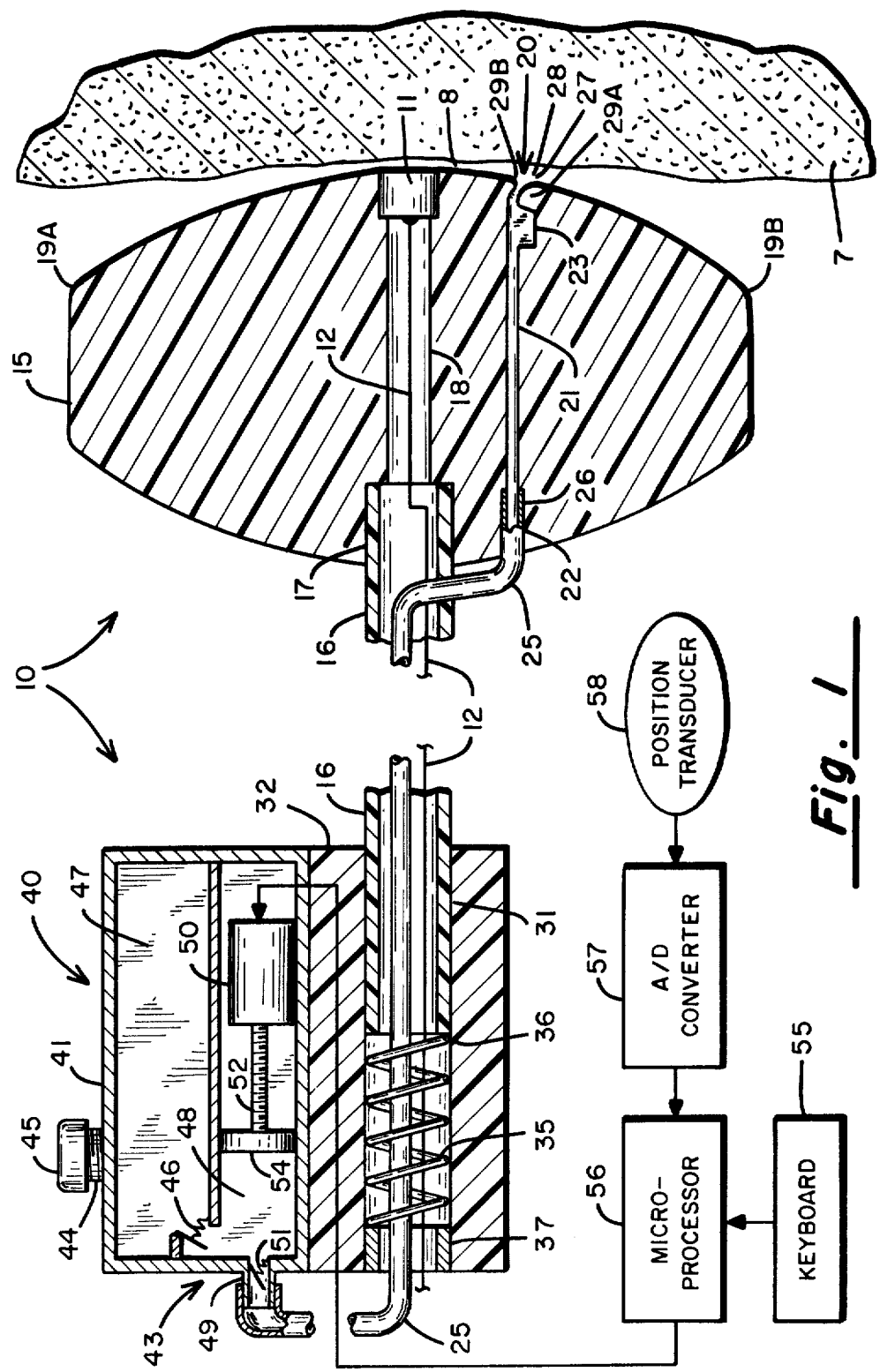
FIG. 1 is a partially cross-sectioned side view of the preferred embodiment of an ultrasonic transducer module according to the invention.
Figure 2:
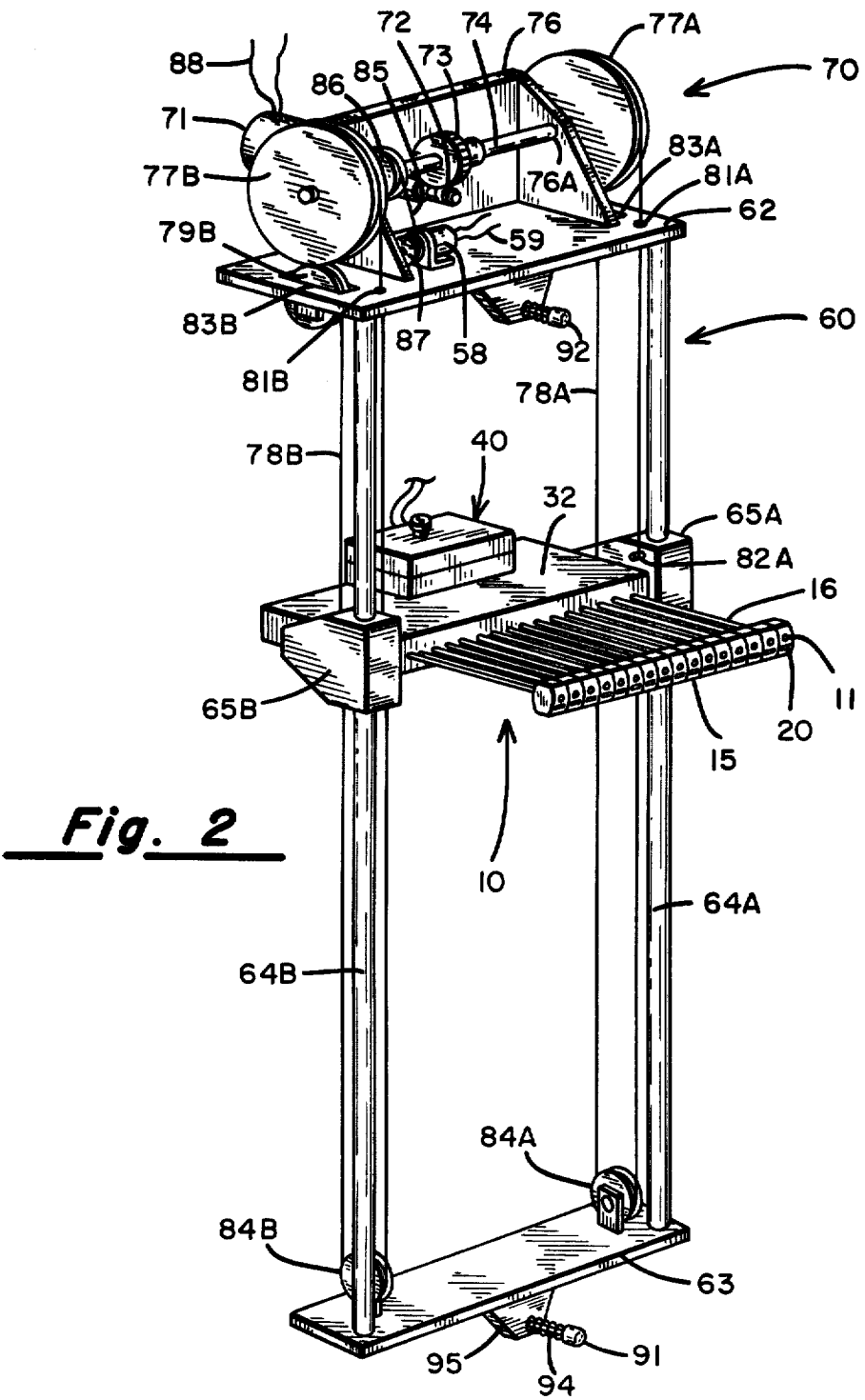
FIG. 2 is a perspective view of an ultrasonic imaging transporter system according to the invention.

A partially cutaway side view of a transducer module 10 according to the invention is shown in FIG. 1. In FIG. 2, there is shown a transport 60 for moving transducer module 10 along the back of a patient. As module 10 moves along the back, position transducer 58 measures the amount of motion and produces an electrical signal representative of the motion. The signal is converted into a digital signal in A/D converter 57 and applied to microprocessor 56. Pulses from microprocessor 56 are applied to motor 50 to drive pump 43. Pump 43 pumps an amount of fluid proportional to the amount of motion of module 10 along the human back 7 through tube 25 to dispensing means 20 on the exterior of transducer shoe 15. As a transducer shoe 15 moves downward with the module 10, the acoustic coupling fluid is applied along the interface 8 between back 7 and the transducer module 10 thereby providing for predictable and efficient coupling between transducer 11 and back 7.

The preferred embodiment of the transducer module 10 according to the invention, will now be explained in detail with reference to FIG. 1. Transducer element 11 is embedded in the exterior surface of transducer shoe housing 15 and connected to ultrasonic transducer electronics (not shown) by means of wire 12. The electronics, which produces the electric current to drive transducer element 11 and which amplifies and processes the electronic signal created in transducer element 11 by a received ultrasound wave, does not form a part of the present invention and will not be discussed further herein. Shoe 15 is supported by hollow cylindrical plunger rod 16 which fits into a cylindrical bore 17 formed in the back of shoe housing 15. A smaller diameter bore 18 connects the hollow interior of plunger 16 with the back of transducer element 11 and wire 12 passes through this bore 18. The upper and lower edges 19A and 19B of housing 15 are rounded and smooth. An internal passage 21 in housing 15 connects another cylindrical bore 22 with acoustic fluid well 23 formed in the front portion of housing 15. Tube 25 fits into bore 22 and a hollow cylindrical collar 26 is fitted within the interior of the end of tube 25, to prevent the collapse of the tube and to urge the outer surface of tube 25 against the inner surface of bore 22. Well 23 communicates with channel 27 in the exterior face of shoe housing 15 through a series of openings such as 28 (more distinctly visible in FIG. 3). Edges 29A and 29B of channel 27 are also rounded and smooth. Plunger 16 fits into a cylindrical bore 31 in rectangular housing platform 32. A spring 35 fits within bore 31 and abuts the rearend 36 of plunger 16. Spring 35 seats against hollow cylindrical collar 37 which is secured in and partially closes the rearend of bore 31. Tube 25 and wire 12 pass through plunger 16 and out the back of housing platform 32. In this embodiment, acoustic fluid source 40 is formed in the top of housing platform 32. Source 40 includes an acoustic fluid reservoir tank 41 and fluid pump 43. Tank 41 has an inlet port 44 which is threaded on its outside surface and which is normally covered by removable threaded cap 45. One-way valve 46 communicates between the interior 47 of tank 41 and pump chamber 48. Outlet port 49 is a hollow cylinder in one wall of pump chamber 48 and has an outlet one-way valve 51 which controls flow through the outlet 49. Tube 25 fits about the outer diameter of cylindrical port 49. Servo motor 50 drives screw 52 which is attached to piston head 54. When piston 54 moves to the right in the drawing, one-way valve 49 closes and one-way valve 46 opens to permit fluid to flow from tank 41 into pump chamber 48 When piston 54 moves to the left, one-way valve 46 closes and one-way valve 51 opens to permit the fluid to flow through tube 25 into well 23 and out into channel 27. Servo motor 50 is electrically connected to, and controlled by microprocessor 56. Position transducer 58 measures the position of ultrasonic module 10 (see the discussion below). Position transducer 58 is connected to A/D converter 57 which is, in turn, connected to microprocessor 56 to control Servo motor 50. A keyboard 55 is connected to microprocessor 56 for controlling the system.

A transporter 60 for moving the ultrasonic module 10 along a transducer/body interface 8 is shown in FIG. 2. As can be seen from this figure, in the preferred embodiment, there are sixteen of the transducer shoes, such as 15. It is evident that there can be any number of shoes, depending upon the surface to be scanned and the scanning procedures, and the invention does not depend upon any particular number of shoes. Transporter 60 includes a frame top plate 62 and a frame base plate 63 separated and connected by a pair of rails 64A and 64B. Rails 64A and 64B pass through cylindrical bores within transducer module blocks 65A and 65B respectively. The bore in blocks 65A and 65B is just slightly larger than the diameter of rails 64A and 64B so that the blocks 65A and 65B slide easily on their respective rails. Module platform 32 is secured to either side of blocks 65A and 65B so that the whole transducer module 10 moves as a unit on rails 64A and 64B. The major portions of the drive system 70 for moving the ultrasonic module 10 is mounted on top plate 62. Drive means 70 includes motor 71 which drives a worm and wheel gear (72 and 73 respectively). Wheel 73 is supported by and locked to axle 74 which is, in turn, supported on frame 76 and turns in bushings 76A and 76B (not shown) in frame 76. Grooved drums 77A and 77B are connected to either end of axle 74 and turn with axle 74. A pair of cables 78A and 78B seat in the grooves of drums 77A and 77B respectively, pass through holes 81A and 81B respectively in top plate 62 and are fastened to pins 82A and 82B (not shown) set in block 65A and 65B respectively. The other end of cables 78A and 78B pass over guide pulleys 79A and 79B (not shown) mounted in slots 83A and 83B in plate 62, then pass under pulleys 84A and 84B mounted on the base plate 63 and return upward to fasten to pins (not shown) secured to blocks 65A and 65B respectively.

Position transducer 58 is mounted on top plate 62 and is driven by position transducer drive belt 85 which rotates about position transducer drive pulley 86 which is secured to axle 74. Drive belt 85 also passes about pulley 87 which is fastened to the drive shaft of position transducer 58. The position transducer 58 is a potentiometer connected nominally across 0 to 12 volt dc (typical operating range 2-8 volts dc). As pulley 87 turns, a wiper within the potentiometer 58 moves and produces a voltage proportional to the distance that ultrasonic transducer module 10, and the various parts of it including dispensing means 20 and transducer element 11, has moved. Wires 59 which carry output signal of position transducer 58 and wires 88 which carry the input current to motor 71 connect to microprocessor 56 (not shown in FIG. 2). Attached to top plate 62 is a means 92 for referencing a first fixed point on the back, such as the spinous process of the seventh cervical vertebrae and a means 91 for referencing a second fixed point on the back 7, such as the sacral crest. These means 91 and 92 are stops supported in brackets, such as 95, with springs 94 providing a bias force between the stops, such as 91, and the brackets, such as 95.

An alternative embodiment of an ultrasonic imaging module 110 according to the invention is shown in FIG. 4. In use, the end 111 of the module is placed against the surface of the object to be ulrasonically scanned, which, for the purposes of this disclosure, shall be the skin 114 of a patient. As can be seen in FIG. 5, when the end 111 of the module 110 is placed against the skin 114 of the patient, roller-ball 112 makes contact with the skin 114. As roller-ball 112 rolls against the surface of skin 114, acoustic coupling fluid flows from fluid reservoir 115 through hose 116, through the interior 127 of housing 117 and clings to the surface of roller-ball 112 while passing through small channel 118 between the roller-ball 112 and bearing surface 122, and thence is transferred to surface of skin 114 by roller-ball 112. Wires 119 connect module 110 to electronic circuitry for ultrasonic imaging (not shown).

Turning now to a more detailed description of the structure of the alternative embodiment of the invention. FIG. 5 shows a cutaway side view of ultrasonic imaging modul 110, disclosing the interior of the housing 117. As can be recognized by FIGS. 4 and 5, housing 117 is in the form of a closed cylinder. At one end 111, walls 121A and 121B are enlarged to form a flange having a bearing surface 122 which defines a portion of the surface of a sphere. Roller-ball 112, shaped in the form of a sphere is mounted in bearing 122; the diameter of roller-ball 112 is slightly smaller than the diameter of bearing surface 122 so that it is free to rotate in the bearing and so that a film of fluid attached to the surface of roller-ball 112 may pass through channel 118 between the surface of bearing 122 and the surface of roller-ball 112. Preferably these diameters are such that channel 118 has a width of approximately 0.010 to 0.030 inches; the optimum dimensions of the channel will depend upon the viscosity of the fluid, which will vary, as known in the art, depending upon the characteristics of the ultrasonic scanning to be performed.

Ultrasonic transducer element 130 is mounted within chamber 127. Transducer element 130 is mounted on the end of hollow cylindrical support rod 132 which is, in turn, supported along the axis of chamber 127 by washer-shaped bracket 133. Bracket 133 has holes such as 134 and 135 through it, which permit acoustic coupling fluid to flow freely within the interior of chamber 127. Wires 119 pass through support rod 132 and attach to transducer element 130 to provide the electrical connection between transducer element 130 and the electronic circuitry for driving transducer element 130 and for amplifying and processing the electronic pulses produced by transducer element 130 when ultrasonic energy impinges upon it. In the embodiment shown, ultrasonic lens 136 is bonded to transducer element 130, although in other embodiments it may be supported by its own bracket within chamber 127. Inlet port 125, which is a short hollow cylinder formed in the surface of housing 117 communicates with opening 126 in housing 117. Hose 116 has an internal diameter such that it fits tightly about the cylinder 125; a clamp may be used to hold tube 116 on cylinder 125, if desirable.

Hose 116 connects chamber 127 with a fluid reservoir 115, which may be any conventional source of pressurized fluid, such as aerosol pressurized container, a compressible bladder filled with fluid, a pump or, in one embodiment even a conventinal water faucet. In the alternative embodiment a reservoir pressurized by gas (aerosol) is used since it is convenient and since it has no source of noise connected to it.

The materials out of which the invention is constructed are, for the most part, obvious from the function performed, however, these will briefly described for completeness. Referring to FIG. 2, rails 64A and 64B are preferably made of stainless steel, while plates 62 and 63 and frame 76 are made of aluminum although any suitable metal or hard plastic may be used. Wheels and pulleys, such as 77A, 79B, and 84B may be made of a machinable plastic such as Teflon ®, although any other suitable plastic, metal or other material may be used. Likewise, blocks 65A and 65B and the housings such as 15 and 32 may be made of Teflon ®, or similar plastics, fibers or metals. Plungers, such as 16, and the gears such as 72 and 73 may be made of brass or any other suitable metal or plastic material.

The springs, such as 35, as well as cables 78A and 78B may be made of stainless steel, or any other suitable metal, compressed fiber, etc. Bracket 95 may be made of aluminum, or Teflon ® while reference tip 91 may be made out of rubber, silicone rubber, or other plastics, fibers, etc. The transducer elements, such as 11 and 130 may be made of barium titanate. Transducer elements may be obtained from Harrisonics of Standford, Conn., 06902. Roller-ball 112 and lens 136 may be made of acrylate platic or any other suitable plastic or metal. Housing 117 for the roller-ball transducer, and the tank 41 and pump chamber 43 may be made of ABS plastic or any other suitable plastic or metal material, preferably one that is injection moldable. Rod 132 and bracket 133 may be made of Teflon ® or any other suitable plastic epoxy, or metal, etc. Screw 52 and piston head 54 may be made of brass, stainless steel, ABS plastic or other suitable materials. Tubes such as 25 and 116 may be of silicon rubber, polyurethane, or any other suitable flexible rubber, plastic, or other materials.

The system of FIG. 2 may be operated by raising ultrasonic transducer module 10 to the top of transporter 60 by means of typing appropriate instructions into microprocessor 56 with keyboard 55. Transporter 60 is then placed up against back 7 so that sacral and cervical references 91 and 92 contact their appropriate reference points on the back. With the transporter in this position, the transducer shoe such as 15 and transducer element, such as 11, will be in contact with back 7. Then the scan is started, by appropriate instructions to keyboard 55. As the ultrasonic transducer module 10 begins to move downwards in the scanning process, position transducer 58 detects the motion of module 10 and provides a signal to A/D converter 57 which, in turn, provides a digital signal to microprocessor 56 which, in turn, provides a signal to Servo motor 50 to turn screw 52 and move piston head 54 thereby pumping acoustic coupling fluid to dispensing means 20 in an amount so that an even layer of acoustic coupling fluid is spread across interface 8 as the module 10 moves downwards. Well 23 within dispensing means 20 provides a means for the fluid to distribute itself uniformly along the openings 28 so that all of the openings discharge the same amount of fluid. In the preferred embodiment microprocessor 56 provides a series of pulses in a number directly proportional to the amount of motion detected by position transducer 58 and servo motor 50 is a stepping motor which turns a determined amount each time a pulse is provided by microprocessor 56.

It is evident in this embodiment that the amount of fluid pumped is related to the amount of movement of the transducer element 11 along the interface, and the rate at which fluid is pumped is also related to the rate of motion of the transducer element 11 along the transducer/body interface 8. It is a feature of the invention that since the rate of application is related to the rate of scan or, in other words, the amount of acoustic coupling fluid applied by the system is related to the surface area of the body scanned by the module, then the layer of acoustic coupling fluid spread by the system will be everywhere of the same thickness and thus, the coupling between transducer 11 and the body 7 will be constant, predictable and repeatable.

The ultrasonic transducer module of the alternative embodiment shown in FIGS. 4 and 5 is intended to be moved by hand along the surface of the body, although clearly it could also be mounted in a means for moving as described in the preferred embodiment. As the module 110 is moved over the body 114, roller-ball 112 rotates at a rate and amount proportional to the movement. Thus, this embodiment also dispenses an even amount of acoustic coupling fluid across the body surface, which amount is related to the surface area of the body scanned by the module. Thus, this embodiment also provides for an efficient, constant and repeatable coupling between the transducer ball 112 and the body 114.

There has been described a novel ultrasonic transducer module that provides for uniform application of acoustic coupling fluid to the surface of the body being scanned. While the invention has been described in connection with two particular embodiments, one skilled in the art will appreciate that numerous other embodiments and departures from the embodiments shown may be made without departing from the inventive concept. For example, a wide variety of dispensing means and application systems may be used. Many different forms of regulating means for controlling the flow of fluid may be used; just one such example would be mechanical coupling between pump 43 and a portion of transporter 60. A wide variety of materials, shapes and dimensions of the various parts of the system may be used. In addition, other features may be added to the ultrasonic transducer module while still employing the inventive elements. It is therefore to be understood that, within the scope of the appended claims, the invention may be practiced other than as it has been specifically described.

What is claimed is:

1. An ultrasonic transducer system for scanning a body, the system including a module of the type having a transducer for converting electrical energy to a beam of ultrasonic energy and for converting received ultrasonic energy to electrical signals and a means for conducting electrical energy to said transducer, said transducer being supported in a housing, the system characterized by:
    a source of acoustic coupling fluid;
    means connected to said source and located on the exterior of said housing for dispensing said fluid;
    means responsive to movement of said means for dispensing along the transducer/body interface for producing a signal representative of said movement; and
    means responsive to said signal for controlling the flow of fluid between said source and said means for dispensing.

2. An ultrasonic transducer system as in claim 1 wherein said means for applying comprises a means for applying said fluid at a rate related to a rate of motion of said transducer along the transducer/body interface.

3. An ultrasonic transducer system as in claim 1 wherein said means for dispensing includes:
    a bearing mounted on said housing;
    a sphere mounted in said bearing; and
    said means for regulating includes:
        a chamber within said housing for containing said fluid, said sphere forming a portion of the wall of said container; and
        a channel between said bearing and said sphere of a size such that said fluid does not pass through said channel when said sphere is not rotating and said fluid passes through said channel when said sphere rotates.

4. An ultrasonic transducer system as in claim 1 wherein said means for regulating includes a computer.

5. An ultrasonic transducer system as in claim 1 wherein said means for regulating includes a pump for pumping said fluid from said reservoir to said means for dispensing.

6. An ultrasonic transducer system as in claim 1 wherein said means for producing a signal includes a position transducer and an A/D converter, and said means for controlling comprises:
    a microprocessor responsive to said signal for producing a plurality of electrical pulses;
    a pump for pumping said fluid from said reservoir to said means for dispensing; and
    a stepping motor responsive to said pulses for driving said pump.

* * * * *